United States Patent
Klein et al.

[11] Patent Number: 5,341,513
[45] Date of Patent: Aug. 30, 1994

[54] MEDICAL SHIELD WITH HEADLIGHT MOUNTING

[75] Inventors: Walter F. Klein; Ira J. Cooper; Leon M. Cooper, all of Lexington, Ky.

[73] Assignee: B. F. Wehmer, Medical Instrument Division, Lexington, Ky.

[21] Appl. No.: 860,899

[22] Filed: Mar. 31, 1992

[51] Int. Cl.⁵ ............................................ A41D 13/00
[52] U.S. Cl. ................................. 2/9; 128/857; 362/105; 2/209.13
[58] Field of Search ............... 128/380, 857, 858, 863, 128/6, 7, 23; 362/105, 106, 103; 2/9, 10, 11, 15, 209.2, 424, 422

[56] References Cited

U.S. PATENT DOCUMENTS

| | | | |
|---|---|---|---|
| 902,216 | 10/1908 | Drager | 362/106 |
| 1,481,224 | 1/1924 | Pimienta | 362/105 |
| 4,195,328 | 3/1980 | Harris, Jr. | 362/106 |
| 4,616,257 | 10/1986 | Kloots | 362/105 X |
| 4,701,965 | 10/1987 | Landis | 128/857 |
| 4,794,496 | 12/1988 | Lanes et al. | 362/105 |
| 4,848,322 | 7/1989 | Dash et al. | 128/857 |
| 4,852,186 | 8/1989 | Landis | 2/9 |
| 4,852,878 | 5/1989 | Kuntz et al. | 128/857 |
| 4,856,535 | 8/1989 | Forbes | 128/857 |
| 4,864,653 | 9/1989 | Landis | 2/9 |
| 4,867,178 | 9/1989 | Smith | 2/9 X |
| 4,884,296 | 12/1989 | Nix, Jr. | 2/11 |
| 4,920,576 | 5/1990 | Landis | 2/9 |
| 4,944,312 | 7/1990 | Smith | 2/9 |
| 4,945,573 | 8/1990 | Landis | 2/9 |
| 4,965,887 | 10/1990 | Paoluccio et al. | 2/9 |
| 4,972,521 | 11/1990 | Lison | 2/9 |

Primary Examiner—Clifford D. Crowder
Assistant Examiner—Larry D. Worrell, Sr.
Attorney, Agent, or Firm—King and Schickli

[57] ABSTRACT

A protective shield is provided for secure mounting on a headlight assembly that is to be supported on the head of a user. The shield is formed of a thin sheet of flexible plastic with a mounting means that is integral with the sheet and including a flexible portion, such as a loop and an aperture. The loop bends into engagement with the top of the housing of the headlight assembly, whereas the aperture fits over the front lens where the light is projected. Tab fasteners on curved wings connected to the upper corners of the shield provide a curl to accommodate the face curvature. In an alternative embodiment for covering only the headlight, a similar mounting arrangement is provided, except at the bottom of the flexible sheet an open loop engages the housing.

5 Claims, 2 Drawing Sheets

ALTERNATE EMBODIMENT

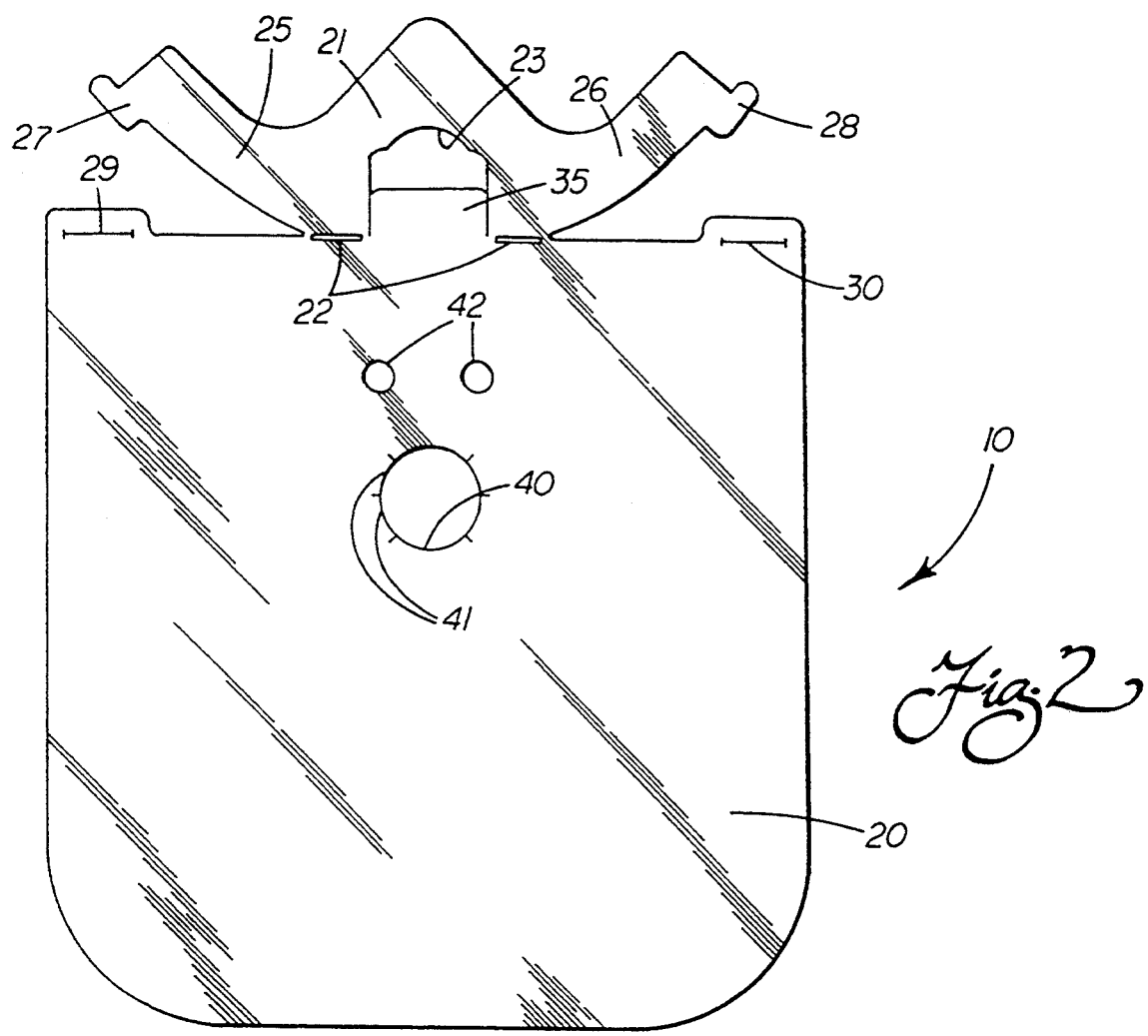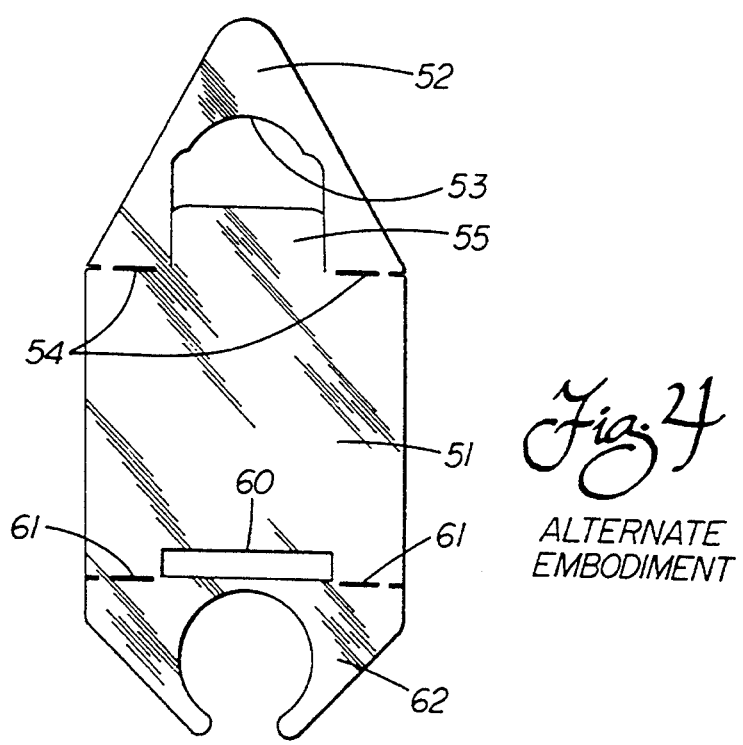

MEDICAL SHIELD WITH HEADLIGHT MOUNTING

TECHNICAL FIELD

The present invention relates generally to protective shields such as may be utilized by surgeons, dentists and other medical personnel and, more particularly, to a disposable shield that is advantageously mounted directly on a headlight assembly supported on the head of the user.

BACKGROUND OF THE INVENTION

In the past, there have been proposed several different types of protective face shields for medical workers. The purpose of the shields is to protect the worker from splatter of fluids from the patient. With the appearance of the AIDS virus, the desire for protection has increased substantially. Today, virtually all surgeons, dentists and other health care workers that are at risk utilize face protection.

The prior art devices usually include a thin plastic sheet positioned over the face of the user. As will be recognized, the manner in which the sheet is mounted so as to be secure, and at the same time not be an obstruction to the operation that is being conducted, is the primary problem to be solved. Past efforts in solving the problem have centered around three general approaches. Probably the most popular approach is to provide a permanent mounting on a separate headband or visor that is placed on the head of the user, such as shown in the U.S. patent to Landis U.S. Pat. No. 4,701,965, issued Oct. 27, 1987. While this approach works well for dentists and some other health workers, it is simply not practical for surgeons and others that need a headlight, or other device that is supported by the head. Securing an additional headband in place, especially where a surgeon's headlight is being used, is difficult at best and is, for all practical purposes, unworkable.

The second approach that is used in some instances is to provide a hand-held shield, such as shown in the Dash et al. U.S. Pat. No. 4,848,322, issued Jul. 18, 1989. As shown in this prior patent, where the shield can be mounted on an endoscope, or the like, it is practical to have a manually supported shield. However, where both hands are needed for the operation being carried out, such as in the case of a surgeon, the hand-held shield is not practical.

The third major effort is where the protective shield is attached directly to the face by adhesive tape or the like, as shown in the Forbes U.S. Pat. No. 4,856,535, issued Aug. 15, 1989. While this approach will work where a headband is used to support a headlight or the like, it has proven to be uncomfortable and generally unreliable. In the instance where an operation is prolonged, the adhesive can loosen, especially due to perspiration that can develop on the forehead of the user as a result of the buildup of heat, such as from the overhead lights.

It is also a concern of surgeons, and others that use headlights, to protect the housing of the headlight from splatter of liquids. It is important to keep the housing clean so as not to harbor an environment for development of bacteria or otherwise support viruses or the like. In some instances of low risk, or where other protection is provided for the face of the user, it is desirable to provide a separate shield for the headlight. This is especially true for headlight designs utilizing ribs around the housing for assisting in dissipation of heat buildup. It is difficult and time consuming to make certain that splattered material in the crevices between the ribs is completely removed after each operation. With a shield in place for the housing, the cleanup effort can be reduced dramatically.

SUMMARY OF THE INVENTION

Accordingly, it is one object of the present invention to provide a protective shield particularly adapted for use with a headlight supported on the head of the user.

It is another and related objective of the present invention to provide an improved face shield that is easily mounted directly on the headlight and also protects the headlight itself from liquid splatter.

Another object of the present invention is to provide a protective face shield that is fabricated of low cost, flexible clear plastic so as to make it disposable, as well as lightweight to improve the comfort to the user.

It is still another object of the present invention to provide a protective shield with mounting means formed by a flexible portion of a thin, flexible sheet and is pre-cut and formed for low cost manufacture and ease of installation on the headlight.

It is still another object of the present invention to provide a protective face shield of the type described, wherein the mounting means for a headlight are integral with the sheet forming the protective shield and additional integral structure is provided for curling the shield to generally conform to the face of the user.

Additional objects, advantages and other novel features of the invention will be set forth in part in the description that follows and in part will become apparent to those skilled in the art upon examination of the following or may be learned with the practice of the invention. The objects and advantages of the invention may be realized and obtained by means of the instrumentalities and combinations particularly pointed out in the appended claims.

To achieve the foregoing and other objects, and in accordance with the purposes of the present invention as described herein, an improved disposable protective shield is provided formed of a thin sheet of clear plastic with integral structure for directly mounting on a headlight assembly supported on the head of a user. The plastic is preferably thin Lexan sheet with a thickness of 0.015 inch. The sheet can be pre-cut and fabricated by a simple punch forming operation, and thus produced at a sufficiently low cost to be disposable after a single use.

The mounting means is preferably a flexible portion of the sheet forming the shield for easy attachment to the headlight assembly by a simple manual bending action. With the arrangement of the present invention, the shield is not only easily mounted, but is held in a very secure manner on the headlight. Of course, the shield can also be easily removed for replacement. To protect the entire face of the user, the sheet extends laterally and downwardly from the headlight assembly sufficient to cover the face. In an alternative embodiment, the shield can be designed to cover the headlight assembly only.

The preferred form of the flexible portion of the mounting means comprises an integral loop positioned at the top of the shield for snapping over the housing of the headlight assembly. The loop is defined by spaced fold lines and a curved tab is formed at the back of the loop for snapping into position. A pair of curved wings extends outwardly from the loop and fasteners are provided to connect the upper corners so as to curl the sheet around the face. In the preferred embodiment, the fastener takes the form of a projecting tab extending through a slit in the upper corner of the sheet. The bottom of the sheet is held in position by a centered aperture with peripheral tabs formed by radial slits snapping over the front lens of the headlight, or in the case of the alternative embodiment by an open loop that snaps around the housing.

An upstanding flap defined by the loop at the top of the sheet protects the top of the headlight housing. A pair of openings are provided to receive the two legs of the positioning bar for the headlight assembly.

In use, the flat formed and pre-cut sheet can be quickly, but at the same time securely mounted on the headlight assembly. First, in the full face embodiment, the projecting tabs of the wings are threaded through the slits at the upper corners of the sheet to form the curl so as to conform to the face of the user. Next, the center aperture is positioned over the front lens of the light so that the peripheral tabs formed by radial slits snap into place. Next, the loop at the top of the sheet is simply pivoted back so as to snap over the top of the headlight assembly. Finally, the two legs of the separate positioning bar are compressed so as to fit through the spaced openings and then released to lock in position on the housing. As for the alternative embodiment, the only variation with respect to the common structure is that the centered aperture is replaced by the open loop that is snapped around the housing. With this simple procedure, the headlight is ready to be positioned on the head of the user for commencing the operation. If the shield must be replaced during an operation, it will be realized that the procedure lends itself to being easily done without removal of the headlight from the head.

Still other objects of the present invention will become apparent to those skilled in this art from the following description wherein there is shown and described a preferred embodiment of this invention, simply by way of illustration of one of the modes best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWING

The accompanying drawing incorporated in and forming a part of the specification, illustrates several aspects of the present invention and together with the description serves to explain the principles of the invention. In the drawing:

FIG. 2 is a plan view of the pre-cut sheet before being attached to the headlight;

FIG. 4 is a plan view of the sheet of the alternative embodiment before attachment.

Reference will now be made in detail to the present preferred and alternative embodiments of the invention, examples of which are illustrated in the accompanying drawings.

DETAILED DESCRIPTION OF THE INVENTION

Figure 1:
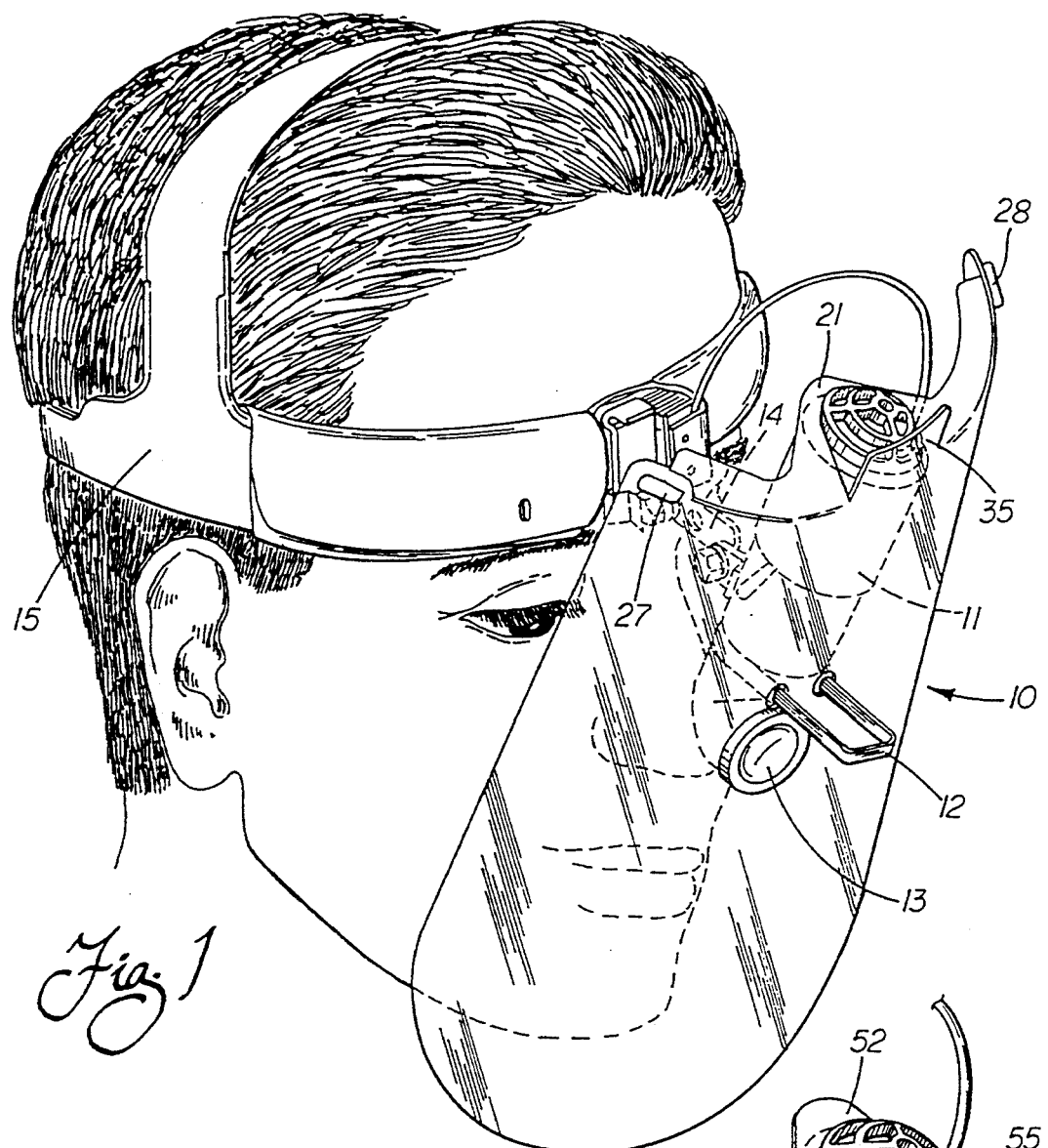
FIG. 1 is a perspective view of a preferred embodiment of the protective shield mounted on a headlight supported on the head of a user.

With reference now to FIG. 1 of the drawings, there is illustrated a protective shield, generally designated by the reference numeral 10, positioned on a headlight assembly 11 in accordance with key principles of the present invention. As illustrated, the headlight assembly 11 includes a positioning bar 12 and a front lens 13 where the beam is projected. The housing of the headlight assembly 11 is attached by a bracket 14 held on a headband 15 positioned on the head of a user, such as a medical worker. It should be understood that the particular headlight assembly 11 is shown strictly for illustrative purposes and that in accordance with the broad aspects of the present invention the protective shield 10 can be adapted for use with other headlights.

As shown in FIG. 1, and further illustrated in FIG. 2, the protective shield 10 is preferably formed of a thin sheet 20 of clear, Lexan plastic. For purposes of the present invention, a sheet of 0.015 inch is found to be particularly adapted for carrying out the purposes of the invention. However, other types of materials and/or thicknesses may be adapted for filling of particular needs or preferences. A key point is that the sheet is pre-cut, such as by a punching and stamping operation so as to be very economically manufactured. Because of the low cost of the material and this fabrication method, the protective shield 10 is a disposable item in use. As an operation is being performed, such as by a surgeon, dentist or other medical worker, the face of the user is completely protected from splatters. Once the operation is over, since the shield 10 is disposable, it can be discarded along with other disposable items, thus greatly reducing the chances of transmission of a virus, bacteria or other harmful organism.

A key feature of the protective shield 10 is that a mounting means for attachment to the headlight assembly 11 is made integral with the sheet 20. Thus, a mounting means fulfilling this criteria is formed by a flexible loop 21 positioned along the top of the sheet and substantially centered. A pair of embossed line sections 22 may be formed at the point where the loop joins with the main body of the sheet 20. During use, this loop forms a mounting means for the sheet and is secured to a fixed portion of the headlight assembly by manual bending action along the line sections 22 (see FIG. 1). A flexible tab 23 is formed along the inside of the loop 21 and as the tab engages the upper portion of the housing of the headlight assembly 11, it flexes and forms a secure lock to hold the shield in position (see FIG. 1).

Extending to the sides of the loop 21 is a pair of curved wings 25, 26 having an integral projecting tab 27, 28, respectively, extending from the distal end thereof. The tabs 27, 28 are situated to engage slits 29, 30, respectively, positioned at the upper corners of the sheet 20. When the loop 21 is initially formed by bending down into the attachment position, the tabs 27, 28 can be inserted into the appropriate slits 29, 30 so as to provide a gradual curl across the shield, as shown in FIG. 1. This curvature assists in covering the full face of the user in order to provide maximum protection.

An upstanding flap 35 is defined by the cutout forming the loop 21 and positioned opposite the tab 23. When the protective shield 10 is in position on the headlight assembly 11, the flap 35 extends upwardly to provide protection for the exposed top of the headlight housing.

The bottom of the sheet 20 is secured in position in this first embodiment by a centered aperture 40 for receiving the front lens 13 of the headlight assembly 11. As illustrated, the aperture is formed by a plurality of peripheral tabs 41 formed by radially extending slits. The aperture 40 and the tabs 41 are sized in order to firmly snap over the front lens 13. This provides additional secure engagement of the shield 10 in position on the headlight assembly 11 and covering the face of the user.

A pair of spaced openings 42 are positioned above the aperture 40 in order to receive the positioning bar 12. As is well known, the positioning bar is metal and is sterilized before each operation. The openings 42 provide easy access to the housing so that the user, upon squeezing the legs of the bar together, can move the bar into position with the receiving holes in the housing and, upon release, the positioning bar legs spring into the locked position. During the operation, the surgeon, or other user, grasps the bar 12 to manually position the headlight beam in the proper position. Advantageously, as this is done, the protective shield 10 follows the direction of the light, thus maintaining maximum protection from splatter.

Figure 3:
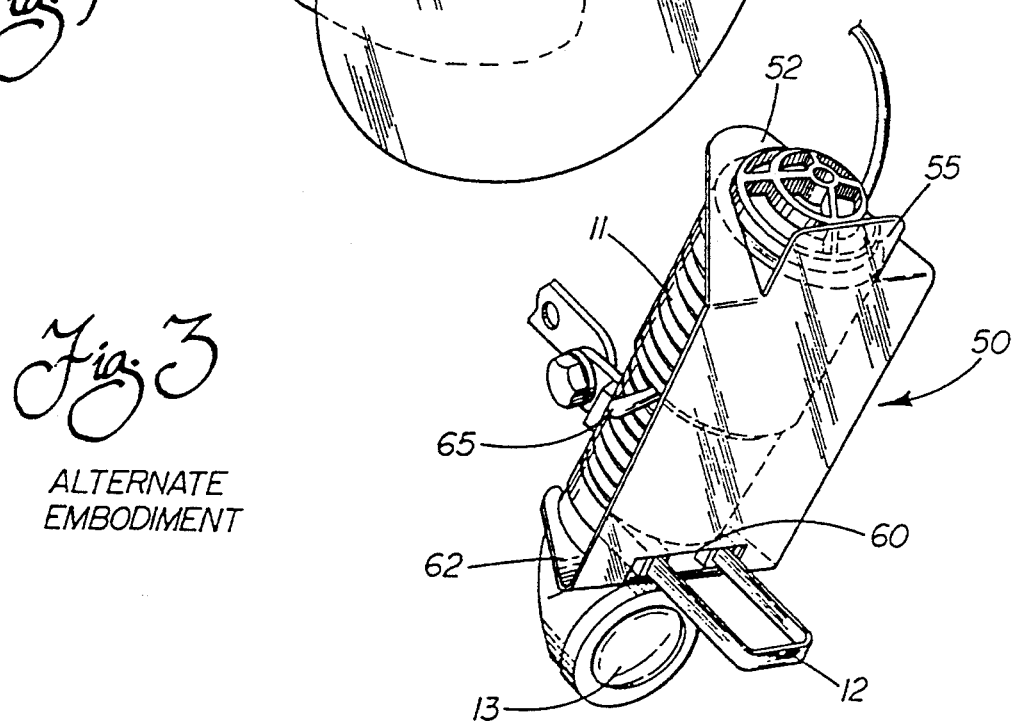
FIG. 3 is an alternative embodiment of the protective shield mounted on a headlight for protection of the headlight housing only.

In the alternative embodiment of FIGS. 3 and 4, a reduced size shield, generally designated by the reference numeral 50, is illustrated. As with the primary embodiment, the shield 50 is pre-cut as a flat sheet, as shown by the sheet 51 in FIG. 4. A loop 52 with a locking tab 53 is integrally pivoted at the top of the sheet along a fold line, that may include embossed segments 54. Also, as in the primary embodiment, an upstanding flap 55 is provided to shield the upper portion of the headlight assembly 11 (see FIG. 3).

Rectangular opening 60 adjacent the bottom of the shield 50 receive the legs of the positioning bar 12. The front lens 13 of the headlight assembly 11 projects below the positioning bar 12. At the bottom of the sheet 51, additional embossed segments 61 may be provided to define an open loop 62 adapted to be bent back so that the arms of the loop snap around the housing, as best shown in FIG. 3. This alternative embodiment is used in situations of lower risk, or where the face of the user is covered by other means. The protective shield 50 does prevent splatter from hitting the housing of the headlight assembly 11 so that cleanup after the operation is greatly reduced, thereby saving time and effort, as well as reducing the chance of harboring harmful viruses or bacteria.

The operation of the headlight assembly 11 is not in any way hampered by positioning of the protective shields 10, 50 on the housing. Indeed, the lightweightness of the sheet 20, 51, its flexibility and the ability for the mounting means to snap into locked position is highly beneficial. The shield 10 is spaced away from the face of the user and the top of the headlight assembly 11 is left open due to employment of the open loop 21 as the mounting means. In this manner, heat buildup is not a problem. As illustrated, an iris lever, such as the lever 65 on the alternative embodiment of FIG. 3, can be easily accessed for adjustment when either embodiment is employed.

In summary, it will now be realized that the use of the protective face shield 10 provides substantial results and advantages over the prior art. The shield is very lightweight and is securely mounted in position by integral components. It can be manufactured very inexpensively by a single punching/stamping operation. The shield incorporates the loop 21 and the centered aperture 40 acting in concert to assure no looseness or possibility of becoming disengaged during an operation. The wings 25, 26 provide an optimum manner in which to provide the curl or curvature to the shield 10 to accommodate the shape of the face of the user.

The alternative embodiment of the shield 50 employs the same basic advantages of flexibility, low cost and ease of use. Regardless of the embodiment used, substantial advantages are obtained over the prior art arrangements where a headlight is being used for the operation.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as is suited to the particular use contemplated. All such modifications and variations are within the scope of the invention as determined by the appended claims when interpreted in accordance with breadth to which they are fairly, legally and equitably entitled.

We claim:

1. A disposable protective shield for a headlight assembly for projecting illumination for external viewing and supported on a user head comprising:
   a thin sheet of flexible clear plastic, said sheet includes top and lateral edges and extends laterally and downwardly sufficient to cover a face portion of the user's head; and
   means for mounting said sheet directly on said headlight assembly;
   said mounting means being integral with said sheet and including separate, spaced dual flexible portions for securing the sheet to a headlight assembly by manual bending action, said flexible portions of said mounting means including an integral loop substantially centered along a top portion of said sheet, spaced fold lines defining said loop, means for attaching said loop to a top of said headlight assembly, a pair of curved wings spaced from the face portion and extending outwardly from said loop, and means for fastening said wings adjacent the top and lateral edges of said sheet to provide a curl to said sheet around the face.

2. The protective shield of claim 1, wherein each curved wing includes a tip and said fastening means includes a projecting tab on each tip and a slit for receiving said tab adjacent an upper corner of the sheet.

3. A disposable protective shield for a headlight assembly for projecting illumination for external viewing supported on a user head comprising:
   a thin sheet of flexible clear plastic; and
   means for mounting said sheet directly on said headlight assembly;
   said mounting means being integral with said sheet and including a flexible portion for securing the sheet to said headlight assembly by manual bending action;

said flexible portion of said mounting means comprising an integral loop substantially centered along a top portion of said sheet, spaced fold lines defining said loop, and means for attaching said loop to said headlight assembly;

said attaching means including a flexible curved tab on said loop for snapping over said headlight assembly;

said mounting means including an additional flexible open loop portion adjacent a bottom area of said sheet for snapping around said headlight assembly.

4. The protective shield of claim 3, wherein said flexible portions are connected to said sheet by embossed lines.

5. A disposable protective shield for a headlight assembly for projecting illumination for external viewing and supported on a user head comprising:

a thin sheet of flexible clear plastic; and means for mounting said sheet directly on said headlight assembly;

said mounting means being integral with said sheet and including a flexible portion for securing the sheet to said headlight assembly by manual bending action;

said flexible portion of said mounting means comprising an integral loop substantially centered along a top portion of said sheet, spaced fold lines defining said loop, and means for attaching said loop to said headlight assembly;

said attaching means including a flexible curved tab on said loop for snapping over said headlight assembly;

said sheet including an upstanding flap defined by said loop for protecting said headlight assembly.

* * * * *